(12) United States Patent
Ivniski et al.

(10) Patent No.: US 9,404,882 B2
(45) Date of Patent: Aug. 2, 2016

(54) METHOD OF PRODUCING A MULTI-MICROCHANNEL, FLOW-THROUGH ELEMENT AND DEVICE USING SAME

(75) Inventors: Dmitri Ivniski, Rego Park, NY (US); Vladimir Shapovalov, Albuquerque, NM (US)

(73) Assignee: New Mexico Tech Research Foundation, Socorro, NM (US)

( * ) Notice: Subject to any disclaimer, the term of this patent is extended or adjusted under 35 U.S.C. 154(b) by 1298 days.

(21) Appl. No.: 12/958,809

(22) Filed: Dec. 2, 2010

(65) Prior Publication Data
US 2012/0032366 A1 Feb. 9, 2012

Related U.S. Application Data

(63) Continuation-in-part of application No. 11/201,699, filed on Aug. 11, 2005, now abandoned.

(51) Int. Cl.
*G01N 27/327* (2006.01)
*C22C 1/08* (2006.01)
*C22B 9/02* (2006.01)

(52) U.S. Cl.
CPC ............. *G01N 27/327* (2013.01); *C22C 1/08* (2013.01); *B22F 2999/00* (2013.01); *C22B 9/023* (2013.01); *C22C 2001/085* (2013.01); *Y02P 10/234* (2015.11)

(58) Field of Classification Search
CPC .................................................. G01N 27/327
USPC ........................................................ 205/775
See application file for complete search history.

(56) References Cited

U.S. PATENT DOCUMENTS

| | | | | |
|---|---|---|---|---|
| 4,187,350 | A * | 2/1980 | McIntyre et al. | 429/533 |
| 4,404,065 | A * | 9/1983 | Matson | 205/780.5 |
| 5,181,549 | A * | 1/1993 | Shapovalov | 164/79 |
| 5,843,767 | A | 12/1998 | Beattie | |
| 6,103,033 | A | 8/2000 | Say et al. | |
| 6,303,924 | B1 * | 10/2001 | Adan | G06F 3/0317 |
| | | | | 250/206.1 |
| 6,638,760 | B1 | 10/2003 | Chen et al. | |
| 6,692,696 | B1 * | 2/2004 | Alberte | 422/50 |
| 7,073,558 | B1 * | 7/2006 | Nakajima | 164/66.1 |
| 2005/0112557 | A1 * | 5/2005 | Liu et al. | 435/5 |
| 2005/0130292 | A1 | 6/2005 | Ahn et al. | |
| 2005/0136500 | A1 * | 6/2005 | Yang et al. | 435/14 |
| 2005/0145364 | A1 | 7/2005 | Nakajima | |

FOREIGN PATENT DOCUMENTS

GB 2289339 11/1995

OTHER PUBLICATIONS

Ivnitski et al., "Non-Invasive Electrochemical Hand-Held Biosensor as Diagnostic Indicator of Dental Diseases" Electrochem. Commun. 5, pp. 225-229 (2003).*

* cited by examiner

*Primary Examiner* — Bryan D. Ripa
(74) *Attorney, Agent, or Firm* — Jennifer S. Stachniak

(57) ABSTRACT

A method of producing a multi-microchannel, flow-through element, including the steps of providing a body of material, and producing multiple microchannels within the body, wherein the microchannels extend through the body to produce a multi-microchannel, flow-through element. Such an element can be used as a micromixer, a sensor element, a filter, a fuel element or a chromatographic element.

11 Claims, 19 Drawing Sheets

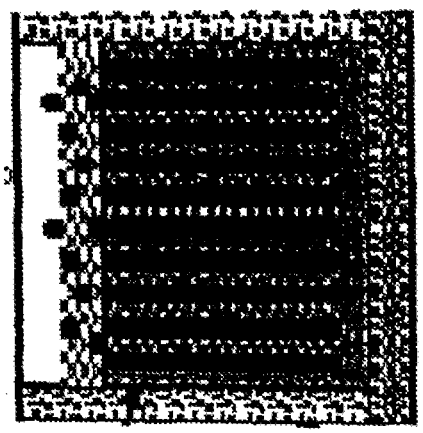
Fig 1c
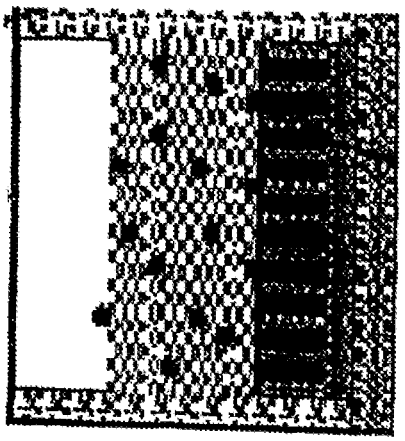
Fig 1b
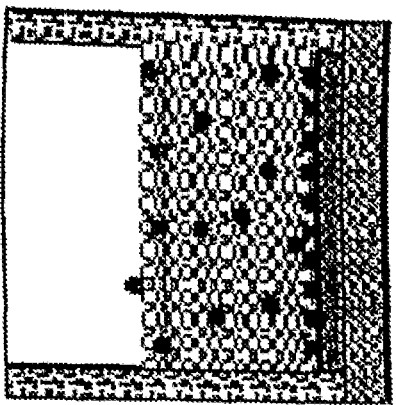
Fig. 1a

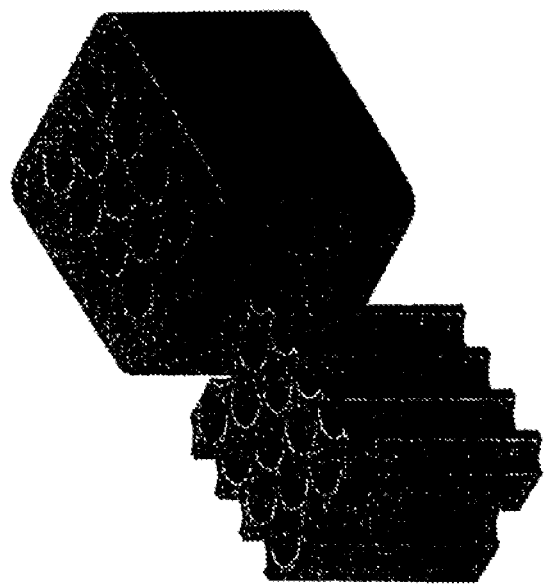

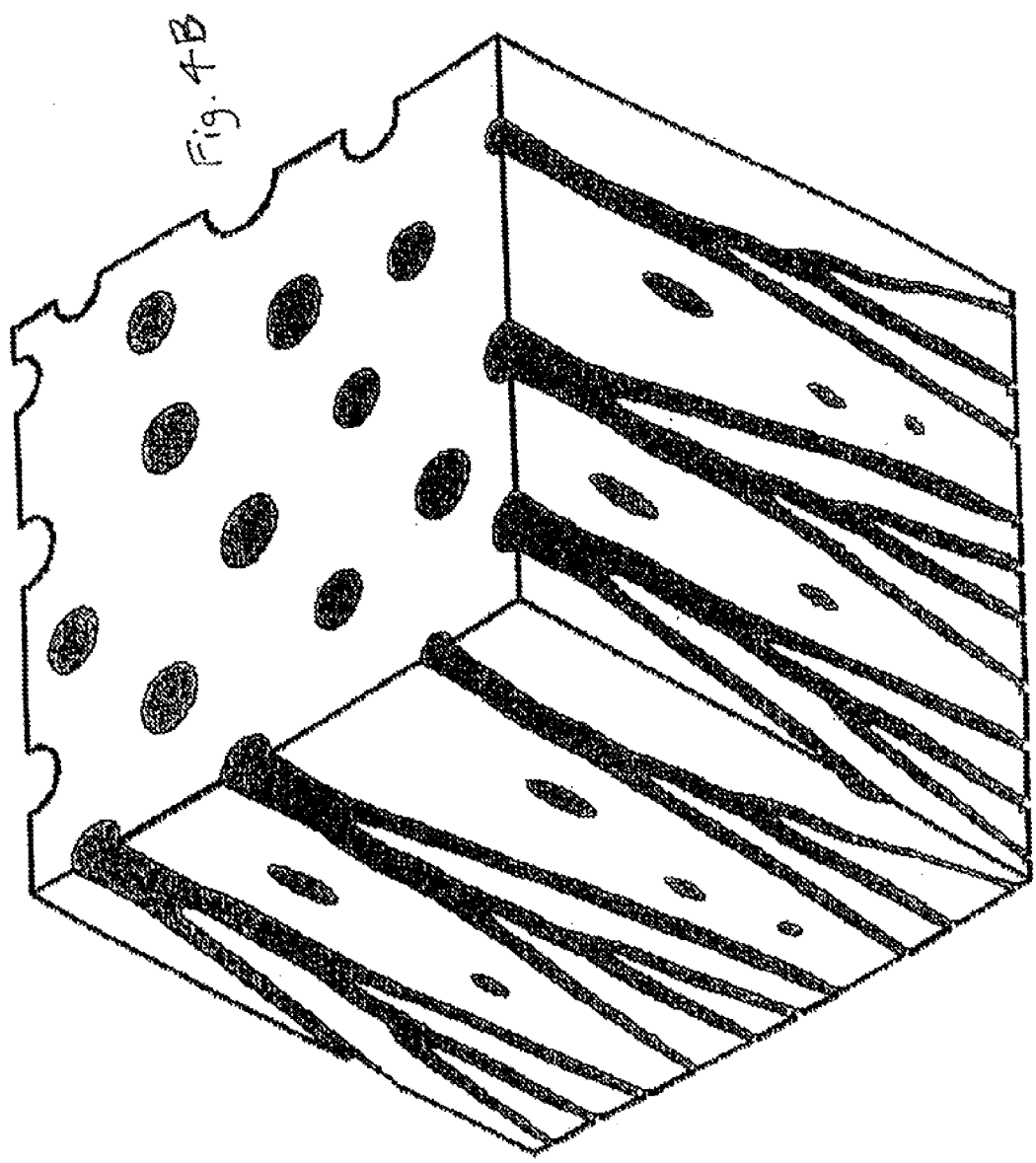

METHOD OF PRODUCING A MULTI-MICROCHANNEL, FLOW-THROUGH ELEMENT AND DEVICE USING SAME

CROSS REFERENCE TO RELATED APPLICATION

The present application is a continuation-in-part of U.S. application Ser. No. 11/201,699, filed Aug. 11, 2005, now abandoned, which is incorporated herein by this reference thereto.

BACKGROUND OF THE INVENTION

The present invention relates to a process for the manufacture of multi-microchannel elements and the use thereof.

Miniaturization is the recent trend in analytical chemistry and life sciences. Similar to advances with integrated circuits in the computer industry, the area of biological and chemical analysis is also undergoing a miniaturization effort. A key benefit of miniaturization is the prospect of integration of all of the steps of an analytical process into a single device. With micron-scale forming, technologies for fluid flows and biosensors are now converging and the way is open for full integration of microfluidics with micro- and even nano-scale biosensors. The range of components that have been miniaturized and used as building blocks for fully-integrated microanalytical systems includes pumps, valves, filters, mixers and reactors, sensors, three-dimensional networks of channels and electronic control circuitry. This will create monolithic structures for combined sampling and measurement, inclusive of special situations where arrays are needed.

Miniaturization of biosensor technologies has intrinsic advantages for improving resolution time (speed of assay), reducing reagent use, and allowing for higher sample throughput. A fusion of micro- and nanotechnology with biology has great potential for the development of low-cost disposable chips for rapid molecular analysis that can be carried out with simple handheld devices. It has been shown that conducting chemical or biological reactions in ultra narrow microchannels or porous materials allows a significant reduction of transport limitations across the unstirred layer (Nemst diffusion layer). The channels manufactured to date have dimensions from 1 to 300 μm and flow speeds in the range up to cm/s. The reduction of physical size of flow cells to cross-sectional dimensions on the order of tens or hundreds of microns (microchannels) results in a large surface area to volume ratio and a decrease of the Nemst diffusion layer from 10 μm to 0.02 μm. In this case, the binding events that occur within the ultra small volume of the microchannels do so with much higher efficiency than in the flow macroscopic systems. Since the magnitude of the diffusionally limited current is inversely proportional to the thickness of the diffusion layer, the effects observed in microchannels may be explained by facilitated diffusion of analytes (antigen, antibody, conjugate, substrate, products of enzymatic reactions, etc.) from the bulk of the solution to the electrode surface. Chips are already being fabricated with picoliter-sized wells and 10-microliter-sized chambers for sample preparation and detection.

Microanalytical devices have found many applications, ranging from the life sciences industries for pharmaceuticals and biomedicine (drug design, delivery and detection, diagnostic devices) to industrial applications of combinatorial synthesis (such as rapid chemical analysis and high throughput screening). Other areas of applications for microdevices for the transport of liquids and gases include fuel cells and optical applications. Miniaturization of biodetectors into a single integrated "lab-on-a-chip" system possesses great potential for environmental monitoring and point-of-care testing, and food analysis, which includes high sensitivity, improved accuracy, lower power and sample consumption, disposability and automation. An emerging demand is to monitor and detect chemical and biological warfare agents in real-time. Fast analysis and on-chip integration of supporting electronic circuitry for signal analysis and remote control would enable sensing at a remote location. The integration of microfluidic transport, total automation and materials handling contributes to a major reduction in system retention and material transfer losses, which reduces sample size requirements and cost of assay. Methods for the parallel in vitro screening of chemical and/or biological compounds are extremely important in drug development, functional proteomics studies, and clinical diagnostics and are used for the parallel screening of families of relative proteins. Current technological approaches which attempt to address this need include cell-based screening systems and microfluidics-based screening systems. Electrochemical microchip systems are particularly useful for this purpose because they easily interface the chemical and biological molecules in solutions with solid-state microelectrodes and can be directly integrated with microelectronics and microfluidic systems to gain advantages in miniaturization, multiplexing, and automation.

Most approaches developed to date are based on the application of two dimensional microchip formats, wherein a suitable set of biological receptor elements (enzyme, antibody, DNA, protein, etc.) are immobilized on the surface of a planar microchip substrate. The diffusion-controlled rate of biospecific reactions can be significantly accelerated in microfluidic systems through the use of microchannels or porous substrates that provide a unique means to prepare a three-dimensional network suited for the immobilization of different biomolecules. Heterogeneous flow-injection bioassays based on microchannel or microporous technologies offer extremely accelerated binding kinetics. First of all, there is a high surface area to volume ratio in the micro channels. Second, the flowing stream actively brings the sample in contact with the solid-phase antibody. This factor results in a greatly enhanced the rate of biospecific interaction (enzyme-substrate, ligand-receptor, antigen-antibody, DNA-DNA, etc.). By engaging the third dimension through organized porous or microchannels in a rigid support material the surface to volume ratio is significantly enhanced.

However, miniaturization and reduction in the volume of the sample analyzed in a microanalytical device have created a problem for analysis because the sample is no longer representative of the bulk specimen. For example, a 1 μL sample containing an analyte at a concentration of 1 fmol/L contains~6000 molecules. Further reduction in sample size to 1 nL leads to a sample containing only 6 molecules of analyte, which may be substantially less than the detection limit of the analytical method formatted into the microchip. Another complication for microanalytical devices is evaporation of microvolumes of sample or reagents from the microchip.

In two dimensional microchip formats the density of receptor spots is ultimately limited by either the dispensing mechanism or the amount of biological recognition material within each spot. This fact negatively impacts the dynamic range and lower detection limit of analysis. The sensitivity of electrochemical detection based on microelectrodes is typically substantially lower then conventional techniques.

Currently, a single microchannel with special inner geometry is individually wired and used in microchip technology. But so far there is a large uncertainty in the test results because of variations in the properties of individual microchannels, i.e., there is no reproducibility of test results.

One of the barriers towards achieving true miniaturized total analysis systems is clogging problems which are related to the size of the microchannels. Micromachined from silicon, glass, plastics, and ceramics, the components have channels with size between 10-20 μm. Bubbles cause significant problems in micro-fluidic system applications. A single bubble can clog a channel that is 100 μm wide or less. Particles cause some of the same problems as bubbles, blocking fluid flow and clogging valves. Particles can enter through the route as well as through the packaging around the injection area. The clogging problems seriously limit the utility of the microfluidic devices. For example, they cannot be used to capture target analyte from samples that contain cellular or large molecule contaminants because the contaminants clog the pores or microchannels of the microfluidic system. Therefore, most biochips are designed for a single use only. Also, many fractionation methods require filters that become clogged over time and contribute to the carryover of particles between tests.

Review of known porous materials (microporous glass, porous silicon, microporous nylon membrane, porous carbon, porous $Al_2O_3$ sol-gel matrix) shows that their common disadvantage is that such structure does not allow good repeatability and reliability of biosensors. The structure usually has a three dimensional porous space including labyrinth and dead-end areas. In addition, the pore surface is rough, the pores have irregular shapes and there is non-uniform distribution in the electrodes. Due to the presence of labyrinths and dead-end areas, target analyte and products of chemical and biochemical reactions can accumulate in the porous electrode. This fact significantly decreases signal/noise ratio, which negatively affects the sensitivity of the assay.

Other limitations are complexity, low production rate, and high cost of known methods for manufacturing microporous and microchannel materials with a desired structure. These drawbacks are raised due to the necessity of involving a considerable number of complex operations involved in the manufacturing process, including having to machine channels into multiple components that then have to be joined together.

An important component in flow-through microchip technology is a micromixer. Rapid mixing is essential in many of the microfluidic systems used in biochemistry analysis, drug delivery and sequencing or synthesis of nucleic acids. Biological process such as cell activation, enzyme reactions and protein folding often involve reactions that require mixing of reactants for initiation. Mixing is necessary in lab-on-a-chip platforms. It is well known that the Reynolds number is low in microfluidic channels, and the flow is laminar under normal conditions. Therefore, the mixing of binary or multi-component fluid streams can be difficult in a microchannel, because it relies on diffusion. In general, micromixers are categorized as active and passive micromixers. Active micromixers use the disturbance generated by an external field for the mixing process. Active mixers can be categorized by the types of external disturbance effects such as pressure, temperature, electrokinetics, magnetohydrodynamics and acoustics. However, with external fields and the corresponding integrated components, the structures of active micromixers are often complicated and require complex fabrication processes. Furthermore, external power sources are needed for the operation of active micromixers. Thus, the integration of active mixers in a microfluidic system is both challenging and expensive. In contrast, passive micromixers do not require external energy; the mixing process relies entirely on diffusion or chaotic advection. Due to the dominating laminar flow on the microscale, mixing in passive micromixers relies mainly on molecular diffusion and chaotic advection.

The microscale passive mixing is a challenge because small channel dimensions make it difficult to create turbulence. In the microchannels liquids lose the assist that turbulence gives to mixing. The reason is that in laminar flow fluid laminae slide over each other and there is no turbulence. Typically, liquid flow in microfluidic devices has very low Reynolds numbers and molecular diffusion is responsible for the mixing and requires a long time to accomplish thorough mixing. The channel walls exert a drag on the liquid, so that fluid at the center of the channel moves faster that at the edge and concentrated samples quickly become smeared. At the microfluidic level, two liquids traveling side-by-side through a narrow channel only become fully mixed after many centimeters (>50 cm).

Currently, the fabrication of micromixers is based on technologies of micro electromechanical systems. The basic substrate materials are silicon, glass, and polymers. The basic design is a long microchannel with two inlets to its geometry; these designs are called the T-mixer or Y-mixer. Since the basic T-mixer entirely depends on molecular diffusion, a long mixing channel is needed. A recent simple method to reduce the mixing path is to make a narrow mixing channel, realizing parallel lamination with multiple streams. This mixer type was successfully used in a practical analysis. However, the limitation is that the fabrication processes is often complicated and expensive; it requires a complex multi step procedure.

In view of the foregoing, it is an object of the present application to avoid the aforementioned drawbacks, and therefore to provide a method of producing a multi-microchannel, flow-through element that, among other features, significantly improves assay sensitivity and the reproducibility of results.

SUMMARY OF THE INVENTION

The method of the present application for producing a multi-microchannel, flow-through element includes the steps of providing a body of material, and producing multiple microchannels within the body, wherein the microchannels extend through the body to produce the multi-microchannel, flow-through element.

The multi-microchannel element produced in this manner can be used, for example, as a micromixer, a sensor element, a filter, a fuel element, or a chromatographic element. If the element is used as a micromixer, the walls of at least some of the microchannels have a non-uniform cross section. Furthermore, the microchannels can merge into a single, larger microchannel having a non-uniform cross section.

One or more of the multi-microchannel elements produced pursuant to the present application can also be used in an electrochemical sensor, wherein the element is provided as a transducer and is an electrically conductive, metallic element. By way of example only, such an electrochemical sensor can be in the form of a flow-through amperometric, potentiometric, conductometric device or a flow-through microchip.

The multi-microchannel elements produced pursuant to the method of the present application, and the applications for such elements, have a number of benefits over conventional flow-through microfluidic technology. For example, the Nernst diffusion layer is reduced significantly, while at the same time clogging is prevented due to multi-microchannel element application with variations in geometry and shape of the microchannels. This allows for rapid, turbulent mixing of liquids in micromixers utilizing the multi-microchannel element of the present application. Furthermore, such mixing can be accomplished on a micro scale.

Furthermore, the multi-microchannel elements of the present application increase the speed of testing or analysis, and at the same time the sensitivity of assay.

Further specific features of the present application will be described in detail subsequently.

BRIEF DESCRIPTION OF THE DRAWINGS

This object, and other objects and advantages of the present invention, will appear more clearly from the following specification in conjunction with the accompanying schematic drawings, in which:

FIGS. 1a-1c show an exemplary sequence of the method of the present application for producing a multi-microchannel, flow-through element;

FIGS. 2A-2F, 3A, 3B show various exemplary embodiments of multi-microchannel elements pursuant to the present application;

FIG. 4B shows another exemplary embodiment of a multi-microchannel element produced pursuant to the method of the present application;

DESCRIPTION OF SPECIFIC EMBODIMENTS

Figure 2C:
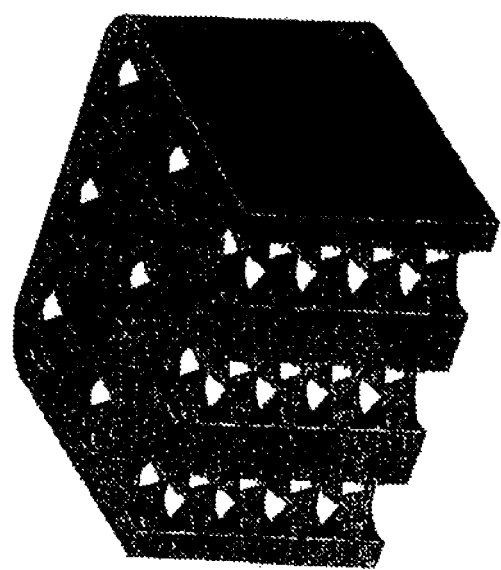

Referring now to the drawings in detail, the method of producing the multi-microchannel, flow-through element of the present application will first be described.

Pursuant to a presently preferred method, the production of such an element is based on the simultaneous decomposition of hydrogen-saturated fluid into solid and gaseous phases at a temperature lower than gas eutectic equilibrium. This produces multi-microchannels, with their specific geometry being determined by hydrogen concentration, direction and rate of solidification, and gas phase pressure at the solidification, as will be described in greater detail subsequently.

One exemplary method of producing a multi-microchannel, flow-through element utilizes an autoclave in which a base material, for example a single body of material, is melted in an atmosphere of a gas containing hydrogen, with the resulting melt being exposed to gas under a partial pressure of between 2.0 and 5.0 atmospheres in order to dissolve at least some of the gas in the melt, with the pressure being increased to from 4.0 to 25.0 atmospheres to enhance dissolving of the gas. The melt is exposed to the gas for a period of time sufficient to allow hydrogen to be dissolved therein and for the concentration thereof to reach a saturation value. This operation will hereinafter be referred to as saturating. After saturating, the melt, which now contains dissolved hydrogen gas therein, fills a mold 1 (see FIG. 1a) that is positioned within the autoclave. Immediately after filling, the pressure within the autoclave is set to a prescribed level, and the melt is cooled. The pressure at which the melt is cooled will hereinafter be referred to as the solidification pressure. As the saturated melt solidifies, the solubility of the dissolved gas displays a sharp decrease. Gas bubbles thus escape from the melt ahead of the solidification front. The gas bubbles grow concurrently with the solidification and do not leave the solidification front, thereby producing microchannels in the solidifying melt. The solidification pressure is controlled as a function of the desired diameter size and microchannel structure. An exemplary sequence showing advancement of the solidification front can be seen in FIGS. 1a, 1b and 1c.

As a consequence of the method described above, which is inspired by the method described in U.S. Pat. No. 5,181,549, the microchannels that are formed extend through the body of material to produce a multi-microchannel flow-through element. However, the microchannels can have a very varied structure with respect to their inner geometry, the number of microchannels, their diameter and shape, their orientation, and the degree of interconnection between the microchannels. These variations are a function of various parameters, such as the hydrogen level in the melt, the gas pressure over the melt during solidification, the direction and rate of heat removal, and the chemical composition of the material of the melt.

Figures 2D, 2E:
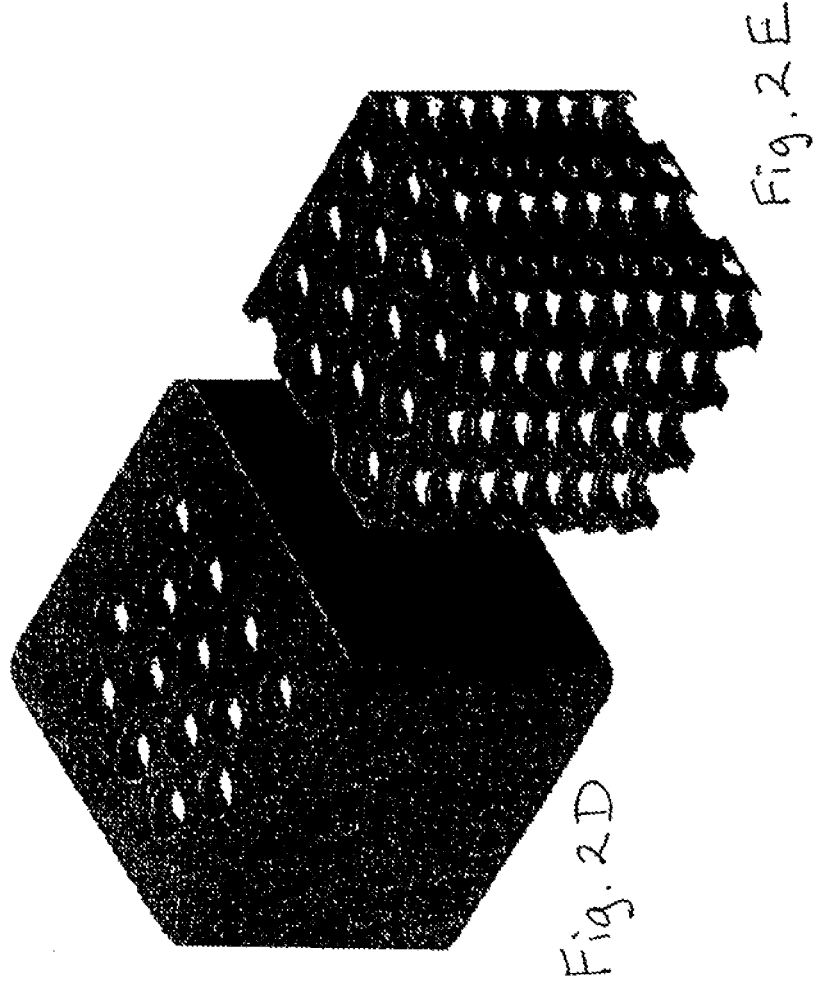
Figure 2F:
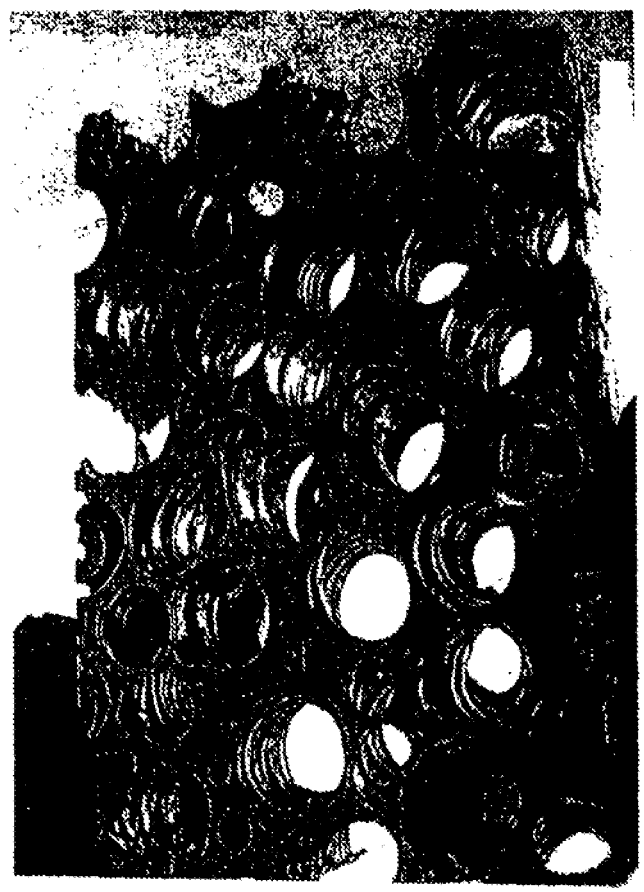

As shown in FIGS. 2A and 2B, the element, which is in the form of a single body of material, can be provided with cylindrical microchannels. To achieve such cylindrical microchannels, the solidification pressure is held constant until solidification has been completed, and the heat is controlled. If a more sophisticated geometrical structure of the microchannels is desired, the solidification pressure is accordingly increased or decreased during solidification. For example, FIG. 2C illustrates cylindrical microchannels having local dendrites on the walls. Such a dendrite structure is created during solidification of the melt with a low hydrogen pressure. FIGS. 2D, 2E and 2F illustrate wavy or corrugated microchannels that are formed by periodically increasing and decreasing the solidification pressure. The wider portions of the channels correspond to lower gas pressures, and the narrower portions correspond to higher gas pressures. Internal pressure fluctuations within a microchannel may also cause repeated widening and narrowing. This can occur when the volumetric rate of gas bubble formation is greater than that of the solidification. The pressure in a microchannel is increased as the bubble expands but drops once the bubble is released. Thus, increasing internal pressure has a similar effect to decreasing pressure above the melt.

Figure 3A:
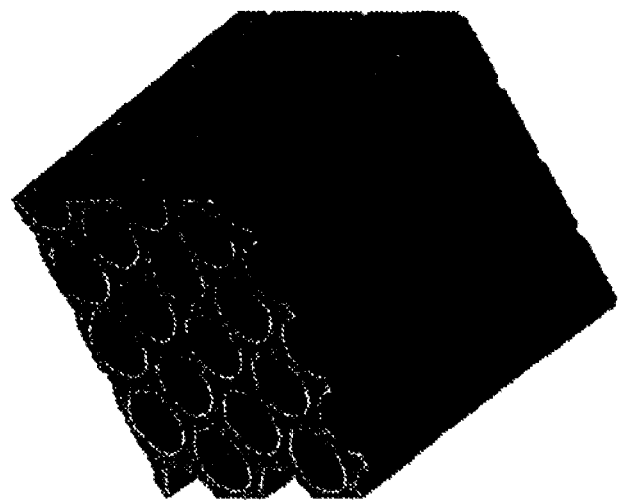

The tapered microchannels of FIG. 3A and the spherical channels of 3B show further possible variations that are produced by appropriate increase or decrease of the solidification pressure during solidification of the melt.

Figure 4A:
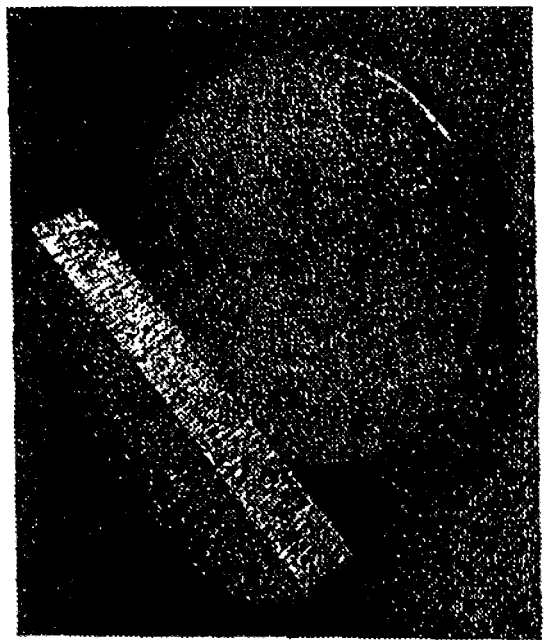
FIG. 4A shows an example of an element produced by the method of the present application.

FIG. 4A shows one example of a finished element. Although all of the microchannels are flow-through channels, since some of the microchannels are disposed at an angle (see also 4B) only a portion of some of the microchannels are visible in the illustrated section. FIG. 4B shows how some of the channels have coalesced to form wider channels. This produces a so-called coarsening of the structure.

From the foregoing, it can be seen that the microchannels of the element of the present application can be uniform, such as being cylindrical, tapered or the like, or can have a non-uniform cross section. For example, the microchannels can contain ridges and grooves or protuberances, or can have periodically or even irregularly changing cross-sections.

The multi-microchannel element of the present application preferably contains a high density of microchannels that provide communication between opposite faces of the element. This is particularly evident in the exemplary product illustrated in FIG. 4A. The microchannels can have an average diameter or cross-section of from 1 to 200 microns.

A wide variety of materials can be used for the body of the element. For example, the material can be Fe, Ni, Co, Cr, Cu, Mg, Mo, W, Al, Au, Ir, Ru, Pd, Pt, Zr, Ti, Rh, alloys thereof, ceramic and glass.

The method of the present application for producing a multi-microchannel, flow-through element will now by described in conjunction with several specific applications.

Figure 5:
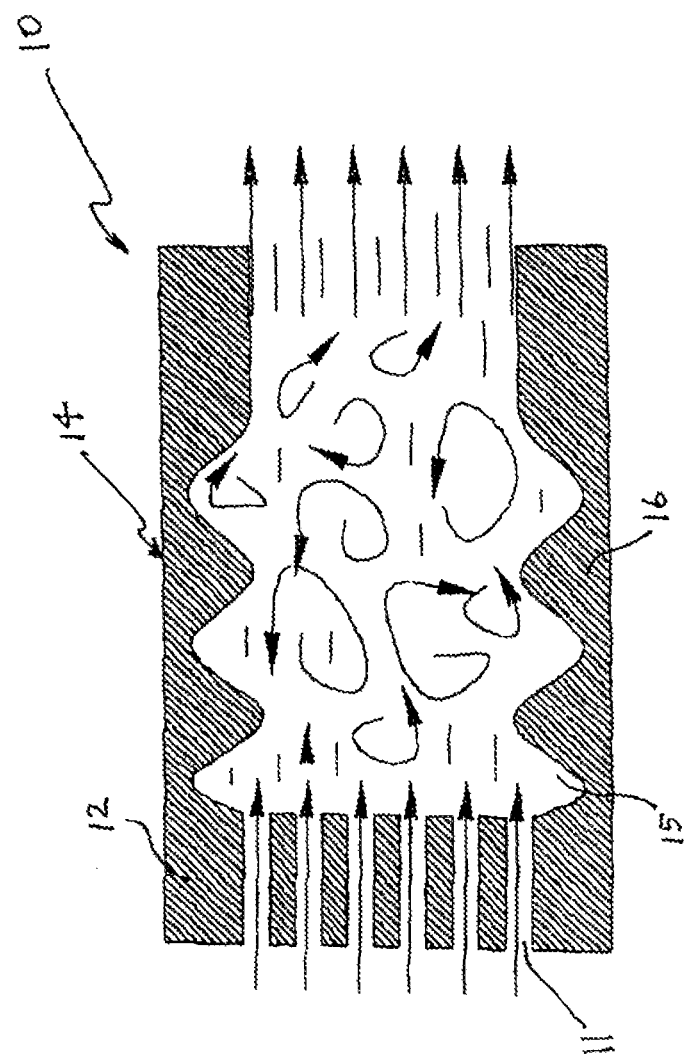
FIG. 5 shows an inventive multi-microchannel element being used as a micromixer.

In one specific embodiment, the multi-microchannel element is used as a micromixer. In particular, FIG. 5 diagrammatically illustrates a passive micromixer 10. Initially, a plurality of microchannels 11 having a diameter of, for example, less than 3 μm are created in a first portion 12 of a body of material 14 under high pressure. Subsequently, the pressure is sharply decreased, and the microchannels 11 are combined to form a single large channel 15 in a second portion 16 of the body of material 14. The channel 15 can have a diameter of, for example, less than 50 μm. By using a pressure pulsation, the solidification pressure is then periodically increased and decreased to create a multi-wave microchannel structure within the large channel 15.

As discussed previously, mixing by diffusion alone is a slow process and requires a low flow rate in order to achieve sufficient mixing. With the design concept of the passive micromixer of the present application, a chaotic advection can be realized due to the modification of the shape and geometry of the channel 15 to achieve splitting, stretching, folding and breaking of the flow there through. This can be seen clearly in FIG. 5, where different fluids are introduced through respective ones of the microchannels 11, then undergo turbulent mixing in the large channel 15, and emerge from the micromixer as a homogeneous mixture. A far greater flow rate through the micromixer is possible as compared to the slow rate required by prior art mixers. Thus, the micromixer 10 makes it possible to achieve a nearly homogeneous mixture in as little as one second, compared with 500 seconds for diffusion alone. It should be noted that although a wave-shaped configuration of the inner wall of the large channel 15 has been illustrated in the micromixer 10 of FIG. 5, other non-uniform cross-sectional shapes of the channel 15 are also possible.

Another possible application for the multi-microchannel element produced by the method of the present application is an electrochemical sensor that utilizes the unique flow-through, multi-microchannel element means, which is provided as a transducer and is an electrically conductive, metallic element.

Figure 6:
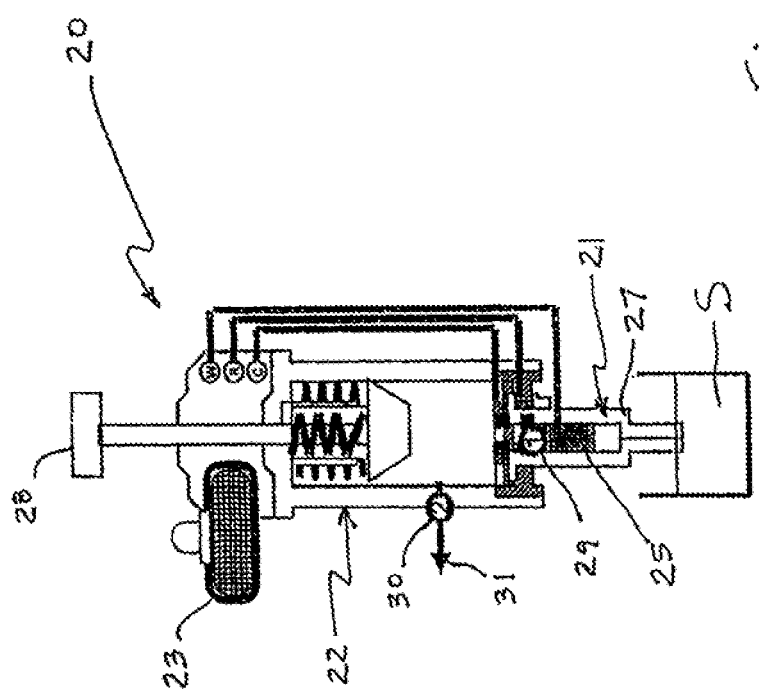
FIG. 6 shows one exemplary embodiment of an inventive multi-microchannel element being used as an electrochemical sensor.

In particular, FIG. 6 illustrates one exemplary embodiment of an inventive amperometric sensor, the general operation of which is known. However, instead of using a known wire working metal electrode, e.g. Pt, Au, Ag, etc., which has the drawbacks discussed previously, the sensor of FIG. 1 has a working electrode in the form of an electrically conductive, flow-through, multi-microchannel element as a transducer, whereby the entire body of the element can be electrically conductive.

In particular, the sensor of FIG. 6, which is indicated generally by the reference numeral 20, comprises a flow-through amperometric detector 21 coupled with a micropipette 22 for injecting a fixed quantity of sample liquid into the flow detector. The sensor also comprises an electronic block 23, which can include an amplifier, a peak detector, a microprocessor, a display, such as a liquid crystal display, and optionally an analog to digital converter. Disposed in the amperometric detector 21, as a working electrode, is the multi-microchannel element 25. This element is connected to the electronic block 23 at W via an appropriate line. A counter electrode, made of platinum wire or the same material as the element 25, is connected to the electronic block 23 at C. Also connected to the electronic block 23 is a reference electrode R, for example an Ag/AgCl reference electrode.

The electrochemical sensor 20 operates as follows. A polarization potential is applied between the multi-microchannel element 25 (the working electrode) and the reference electrode R. To accomplish an electrochemical measurement, a selected volume of sample S containing an analyte is drawn into the capillary tube 27 and the working chamber of the amperometric detector 21 where the working electrode or element 25 is disposed by pressing and immediately releasing the spring-biased plunger 28 of the micropipette 22. A first one-way valve 29 permits flow of the sample S within the multi-microchannel element 25 upwardly from the tip of the capillary tube 27. The injected or drawn-in sample forms a zone within the working electrode or element 25. A second one-way valve 30 allows flow of fluid out of the micropipette 22 via the outlet 31. Thus, when the plunger 28 moves upwardly or is raised, fluid is drawn up into the capillary tube 27 and past the first one-way valve 29, during the course of which the working electrode or element 25 is contacted. When the plunger 28 is pushed down, the valve 29 is closed, forcing the fluid that is disposed in the micropipette 22 above the valve 29 to be discharged through the second one-way valve 30 and out of the outlet 31. Between different measurements the microchannels of the element 25 can be washed with a washing buffer.

The physico-chemical change (current, potential, impedance, etc.) that is produced as a result of specific interactions between target analyte in the sample, and the complementary biorecognition reagent immobilized on the surface of the working electrode or element 25, for example recognition material immobilized on at least some of the microchannels of the element, is detected as a signal. In particular, an electrical signal is produced that can, for example, be shown on the display of the electronic block 23 and that can be correlated to an amount, concentration, or level of an analyte in the sample.

The microchannel of the electrically conductive, flow-through, multi-microchannel element 25 of the present application can, as discussed previously, be made, for example, by the method inspired by the process described in U.S. Pat. No. 5,181,549, Shapovalov. Other approaches for producing the multi-microchannel element 25 are, of course, also possible. For example, laser technology could be utilized.

The base material for the multi-microchannel element can be derived substantially from Fe, Ni, Co, Cr, Cu, Mg, Mo, W, Al, Au, Ir, Ru, Pd, Pt, Zr, Ti, Rh, or alloys thereof. The multi-microchannel element 25 can also have a ceramic base on which the aforementioned metals or alloys thereof can be provided as an electroconductive coating.

In one specific embodiment, the multi-microchannel element 25 is a stainless steel element having the following composition, indicated in % by weight: 0.02C, 10.2Ni, 18.3Cr, 0.03P, 0.02Si, 0.12Co, 0.05Mn, 0.02S, and the remainder Fe.

The shapes of the microchannels of the working electrode or element 25 can vary as required for particular applications. However, in all cases the microchannels provide flow-through between opposite faces of the element 25, whereas there is no fluid flow directly from one microchannel to another within the element 25, although individual microchannels can join together (see, for example, FIG. 4B). The microchannels can, as previously discussed have a cylindrical, conical, ellipsoidal, or more complicated shape, including ridges and grooves to further increase the surface area of a given microchannel. The surfaces of the microchannels can be mirrored and smooth, without polishing, with the same chemical composition at any location. The cross-section of the microchannels can range from 1 to 200 microns.

In the case where the multi-microchannel element is in the form of a working bioelectrode, binding agents, also known as chemical or biological recognition agents, such as proteins, polypeptides, nucleic acids, receptors, polysaccharides, phospholipids, cells, tissue, nano-particles, selected from the group consisting of Au, Ag, Mi, GIS, and carbon nanotubes, with immobilized biological recognition agent, and related unnatural polymers of biological relevance, can be immobilized on at least part of the walls of the microchannels, especially for carrying out binding reactions involving small molecules, macromolecules, particles or cellular systems. Immobilization of the biological binding agents can be effected, for example, by covalent coupling, cross-linking, affinity immobilization, etc.

It should be noted that since the material of the multi-microchannel element 25 of the inventive electrochemical sensor is itself not porous, the microchannels can be easily cleaned so that the sensor can be reused. In addition, this easily allows removal of all contaminants from the microchannels, a situation which is not possible with a porous electrode, due to the labyrinth structure thereof, which makes it very difficult to wash out the contaminants. Therefore, the multi-microchannel element 25 allows a significant decrease of non-specific signals and an increased ratio of signal to noise. This of course applies most specifically to those applications where the microchannels have smooth walls rather than irregular shapes such as ridges and grooves.

Figure 7:
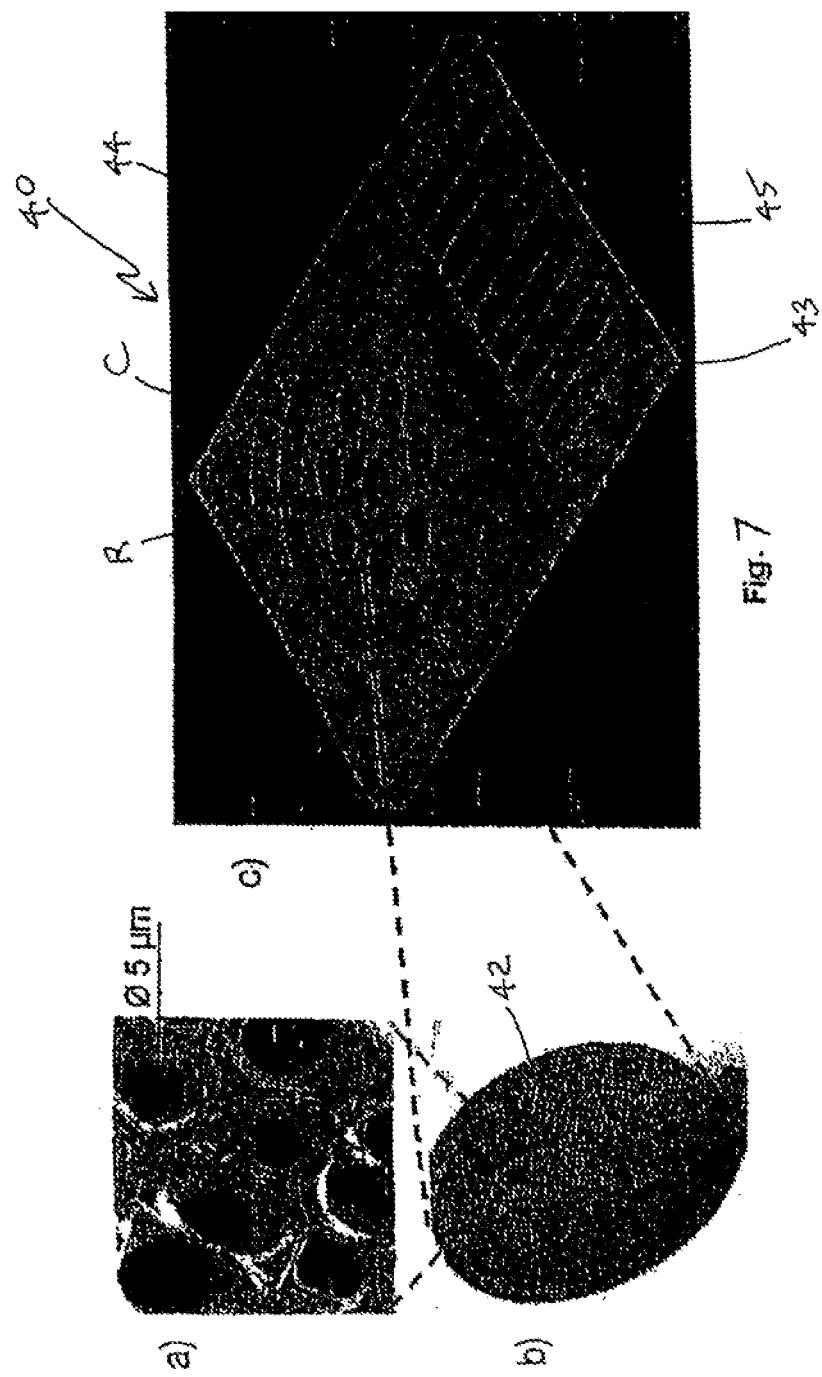
FIG. 7 shows another exemplary embodiment of an electrochemical sensor of the present application with the caps removed to show the plate and sensor/conductor carrier, and also shows enlarged views of an exemplary multi-microchannel element and a few microchannels thereof.
Figure 8:
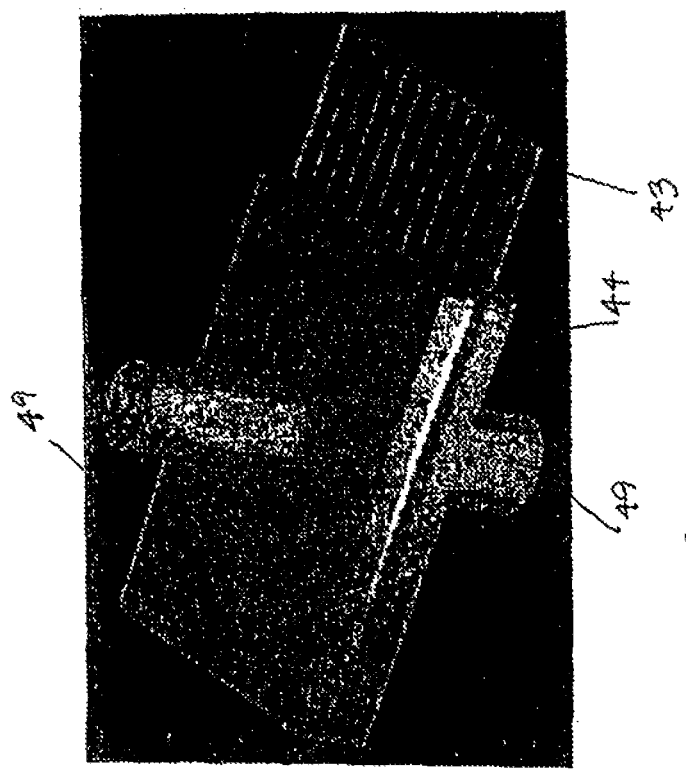
FIG. 8 is a perspective view of the electrochemical sensor of FIG. 7, including caps.
Figure 9:
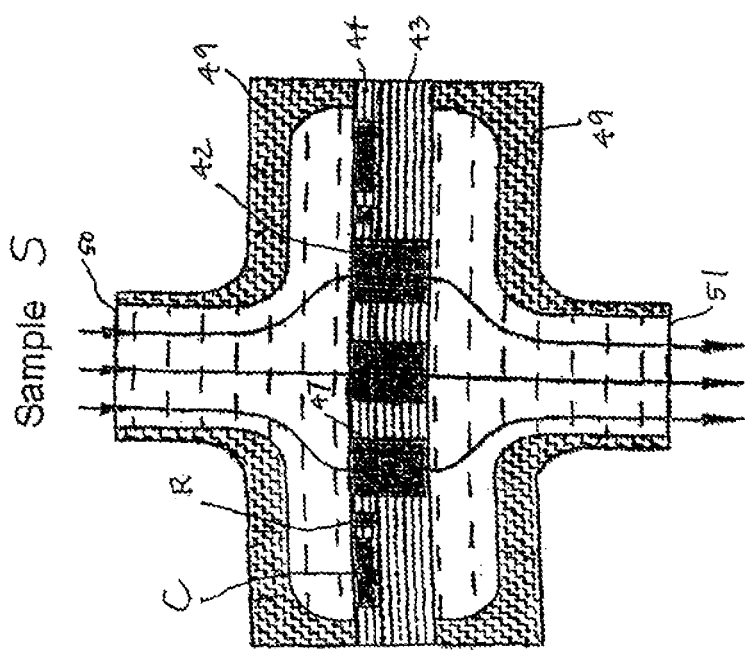
FIG. 9 is a cross-sectional view through the capped portion of the electrochemical sensor of FIG. 8.

FIGS. 7 to 9 illustrate another exemplary embodiment of an inventive electrochemical sensor. In particular, this sensor application is in the form of a flow-through micro-array chip, and is indicated generally by the reference numeral 40. By way of example, the micro-array chip may be 2.0 cm×2.0 cm in size and a few millimeters thick. FIG. 7, in part c) thereof, shows a sensor or micro-array chip 40 without the so-called caps, which will be described in detail in conjunction with FIGS. 8 and 9. The micro-array chip 40 is provided with a plurality or array of working electrodes, each in the form of a flow-through, multi-microchannel electrode or element 42 as a transducer. These multi-microchannel elements or electrodes 42 are held in a sensor or electrode/conductor carrier 43. A plate 44 is disposed on at least part of the carrier 43 (see also FIG. 8) to protect the electrical leads or wires that connect each of the multi-microchannel elements 42 to a respective conductor or contact pad 45 provided on the carrier 43.

The plate 44 is provided with respective holes 47 for receiving that portion of the multi-microchannel element 42 that extends beyond the upper surface of the carrier 43 (see also FIG. 7). Also provided on the plate 44 are a counter electrode C, for example of stainless steel, and a reference electrode R, for example an Ag/AgCl reference electrode. The multi-microchannel elements 42, the counter electrode C, and the reference electrode R are connected by appropriate conductive material, such as a carbon conductive ink, a conducting polymer, or metallic compounds, to respective ones of the contact pads 45 of the carrier 43. The conduct pad 45 is a region which is used for connection with the contacts on the control unit. The contact pads 45 are typically made using the same conductive material, such as a carbon conductive ink, a conducting polymer, or metallic compounds.

One of the multi-microchannels 42 is shown in an enlarged view in part b) of FIG. 7, while a few of the microchannels of the element 42 are shown in part a). By way of example only, these microchannels can have an average diameter of 0.5 to 1.0 microns, with the element 42 having an overall diameter of, for example, 1.0 mm. Each so-called microelectrode may contain, for example, 40 to 100 microchannels. The side walls of the microchannels of the elements 42 can have coated, or immobilized thereon chemical or biological recognition material, i.e. receptors, for example proteins, antibodies, DNA, enzymes, cells, etc.

Figure 3B:
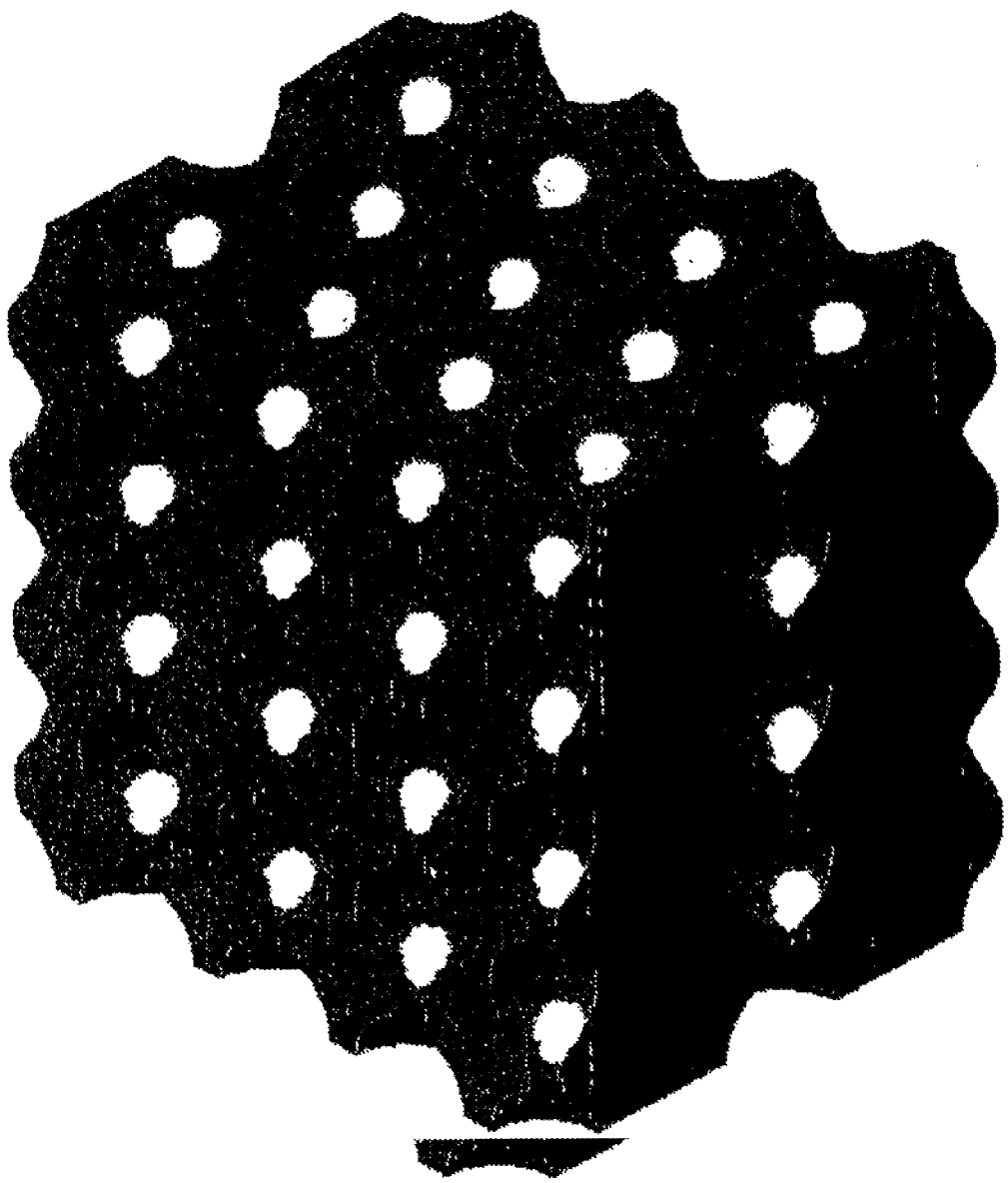

Although in the illustrated embodiment eight multi-microchannel electrodes or elements 42 are shown, any number of elements 42, which can be designed or embodied to sense different substances, can be provided, and can be disposed in any convenient pattern. The elements 42 can have microchannels in the form previously discussed and shown by way of example in FIGS. 2 to 4.

Although the carrier 43 and the plate 44, which can be made primarily of non-conducting materials, including, for example, glass, polymeric or plastic materials and ceramic materials, are shown in the illustrated embodiments as separate components, they could also be a unitary component.

FIGS. 8 and 9 show the flow-through micro-array or biochip 40 of FIG. 7 with caps 49 disposed on opposite sides of the unit comprised of the carrier 43 and the plate 44. These caps 49 can be made primarily of a polymeric material such as polycarbonates, polyesters, polyvinyl chloride, polyamides, or Teflon. As indicated by the arrows in FIG. 9, a sample S is introduced or injected into the inlet 50 of the upper cap 49. The sample S spreads out over the surface of the plate 44, and flows through the microchannels of the various electrodes or elements 42. The sample then exits via the outlet 51.

Analyte (e.g. chemical or biological agent) that is provided in the sample S, and that is related to the sensing layer coated or immobilized on the microchannels of the elements 42, interacts with the chemical or biological recognition agents to produce a signal, which is ultimately displayed as discussed in connection with the embodiment of FIG. 6. For example, amperometric measurements of the output data generated by the electrodes or elements 42 can be measured with a commercially available multi channel potentiostat. The outputs from the potentiostat are fed to a pattern recognition component that is provided with appropriate software, data processing electronics, and electronic interfaces.

The signal pattern from the sensor array is connected to an onboard computer, where initial processing of the data is carried out. The data is then further processed by suitable software for the purpose of signature identification. The responses are analyzed mathematically, using pattern recognition techniques, to differentiate, for example, between different chemical or biological species, including those with closely-related structural characteristics.

A combination of flow-through multi-microchannel recognition elements, with sensor array and sophisticated pattern neural network software program, can provide a basis for design and development cell-based biosensors. The living cells can serve as the molecular recognition elements. Each microelectrode, which is used as a substrate for cell immobilization and for direct measurement of bioelectrical activity of cells, is connected to the multichannel potentiostat and is used as the transducer between the cells and the electronic system to monitor, record, and analyze the cellular response. This makes it possible to get maximum information about how the cell is operating and to understand a mechanism of how cell is responding to the drug, chemical, toxin, or unknown compound.

As a cell-based sensor, the micro-array chip 40 can have a number of applications, such as pharmaceutical screening, environmental monitoring, and the detection of toxins. When appropriately configured, the micro-array chip 40 can be used for monitoring the bioelectrical activity of cultured cells over extended periods of time. Furthermore, since cell-based biosensors make use of direct measurement of physiological functions, and changes induced by toxins, they can be used to analyze unknown agents. This can be useful for pharmaceutical screening, drug discovery and basic neuroscience, as well as for environmental monitoring, such as chemical/biological warfare agents, toxins, metals, ground water contamination, etc.

As known, drug discovery or development can cost from $400 million to $600 million dollars. In this respect, application of cell-based sensors can decrease the time of drug identification or development and can save money for drug discovery or development significantly.

Although the multi-microchannel element of the present application has been described in conjunction with micromixers and sensor elements, it is not limited to such applications. For example, by way of example only, the multi-microchannel element could also be used as a filter element, a fuel element, or a chromatographic element (mixer, column) of gas or liquid chromatographs.

Liquid chromatography (LC) is one of the most widely used techniques for separation and analysis of liquid samples. The components of the sample are separated while flowing through a separation column, and sample components are fixed and identified by referring to a resulting chromatogram. However, conventional chromatographs are bulky and not amenable to use in field conditions. Other practical problems associated with conventional chromatographs include high-solvent consumption and long analysis time. Typically, the time of assay is between 30 and 60 minutes. Thus, portability, speed, and cost are the main driving forces for developing miniaturized chromatographs.

One method by which the size of the chromatograph and the analyzing time of a liquid chromatograph can be decreased significantly is to reduce the size and diameter of the separation column. For example, for a good performance, a separation column must be very narrow (less than 10 micrometers in diameter).

However, reducing the size of the separation column has created a problem, which is related to the high pressure involved in pumping liquids through the single microchannel. Therefore, there is a great need to develop a novel structure of the separation micro-column that address as issues related to decreasing of a pressure drop and increasing to a maximum an active surface area in the microchannel with small diffusion lengths. All of these requirements can be realized by fabrication of separation columns by using the multi-microchannel elements which are presented in the present application. If a flow-through multi-microchannel element is used, the liquid phase carrier experiences very little resistance in the direction of flow and the pressure drop across the multi microchannel element is effectively minimized. In order to separate the components of a sample flowing through the multi-microchannel element, the surfaces of the multi-microchannels can be easily mirrored and smooth and be chemically activated for anion exchange. The flow-through separation column based on application of a multi microchannel element allows much faster mass transfer, and separations of only a few minutes can be achieved for both small and large molecules.

Figure 10:
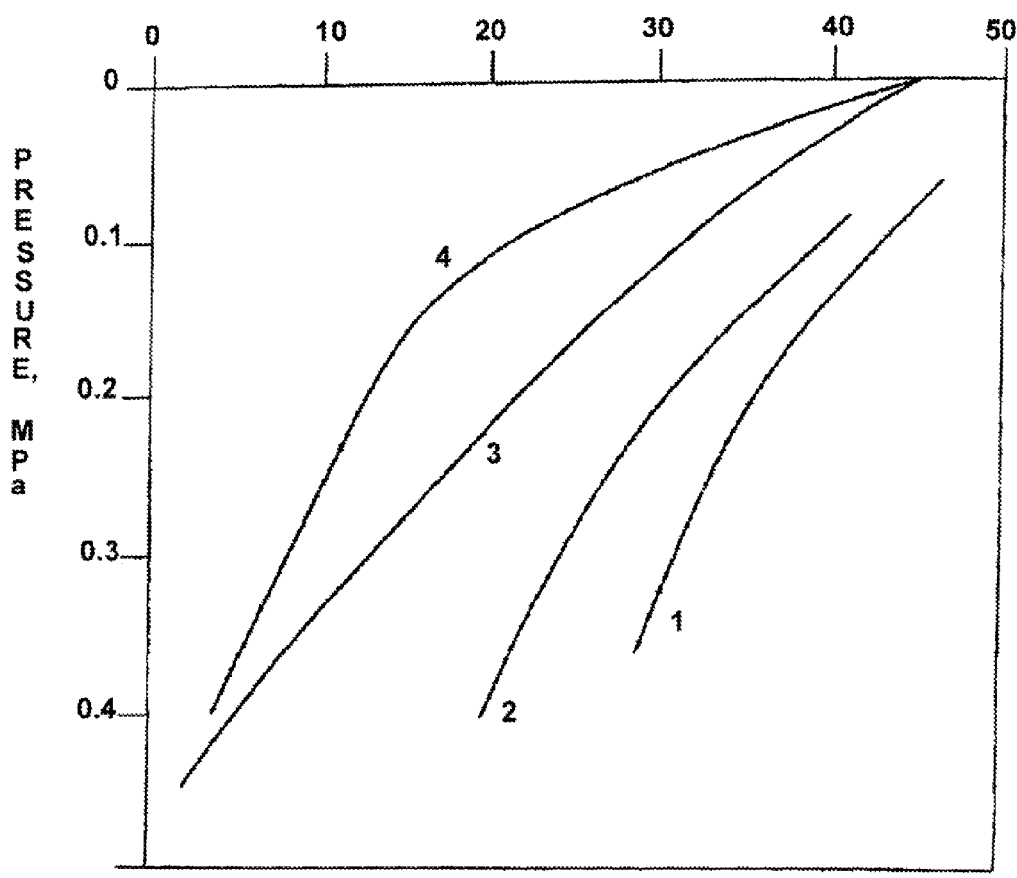
FIG. 10 is a diagram illustrating the influence of pressure on channel diameter inside a copper matrix.

In several trials, total gas pressure was changed below solidifying liquid solution, hydrostatic pressure of solidifying liquid solution was changed above growing bubbles, and surface tension of growing bubbles was changed. It was found that all type of pressures have impact on pore diameter, as illustrated in FIG. 10. Thus, the variation of hydrostatic pressure of solidifying liquid solution above growing bubbles from 0.2 MPa to 0.5 MPa can provide porous matrix with ultra-small channel diameter between 0.0 μm and 10 μm. It is extremely valuable for design and development new generation of a filter or a chromatographic element (mixer, column), biosensor technology and new type of micro size biofuel cells based on direct bioelectrocatalysis.

The solidification pressure included total gas pressure over solidifying liquid solution, hydrostatic pressure of solidifying liquid solution above growing bubbles, and surface tension of growing bubbles. FIG. 10 illustrates the pressure influence on channel diameter inside a copper matrix; line 1 indicates the pressure which is generated by surface tension of growing bubbles, line 2 indicates only total gas pressure over solidifying liquid solution, line 3 indicates only hydrostatic pressure of solidifying liquid solution above growing bubbles, and line 4 indicates the action of all type of pressures simultaneously.

Figure 11:
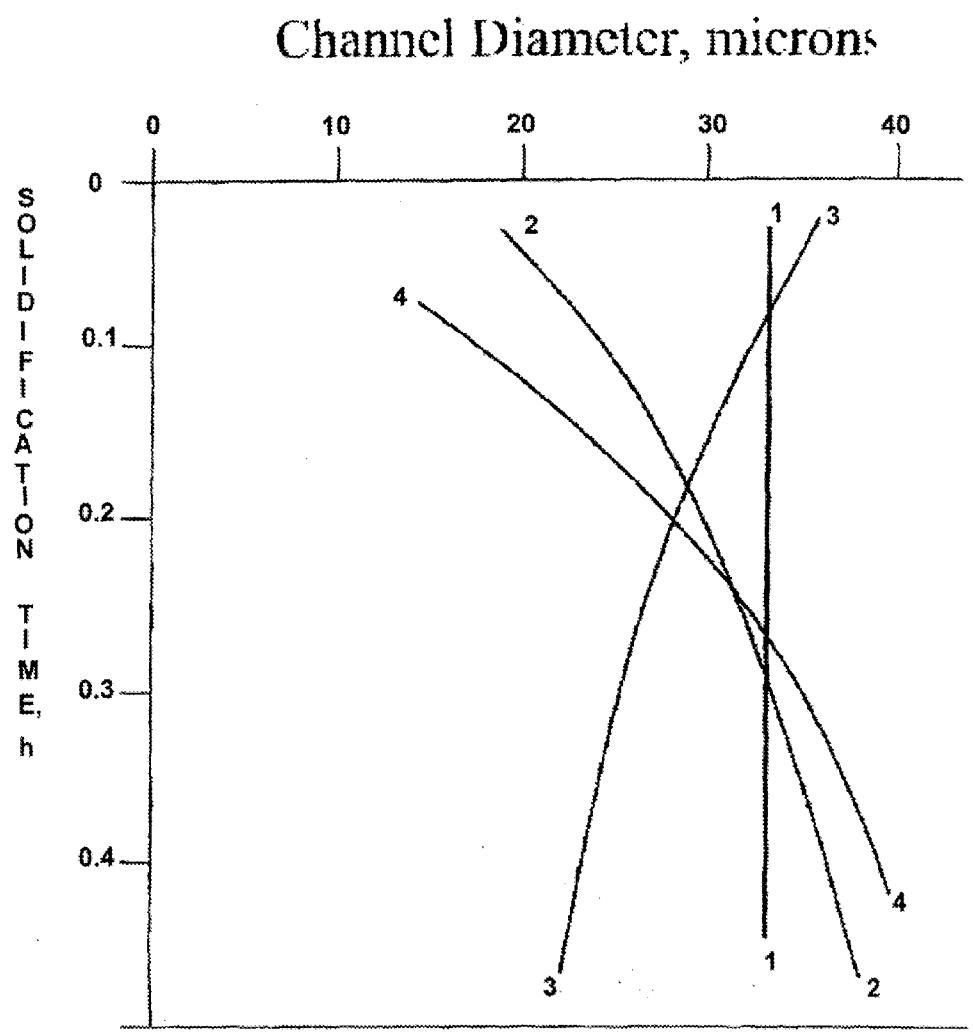
FIG. 11 is a diagram illustrating the change of channel diameter during solidification.

As shown in FIG. 11, solidification pressure, speed and direction were kept constant from the beginning of bubble nucleation to the end of material solidification, resulting in cylindrical microchannels in said elements. FIG. 11 shows the channel diameter changing during solidification. Line 1 indicates that all parameters are constant and solidification is directed to one direction; line 2 indicates that total gas pressure was decreasing; line 3 shows an increase of solidification speed; and line 4 indicates that all parameters are constant but solidification is directed in a radial direction.

Figure 12:
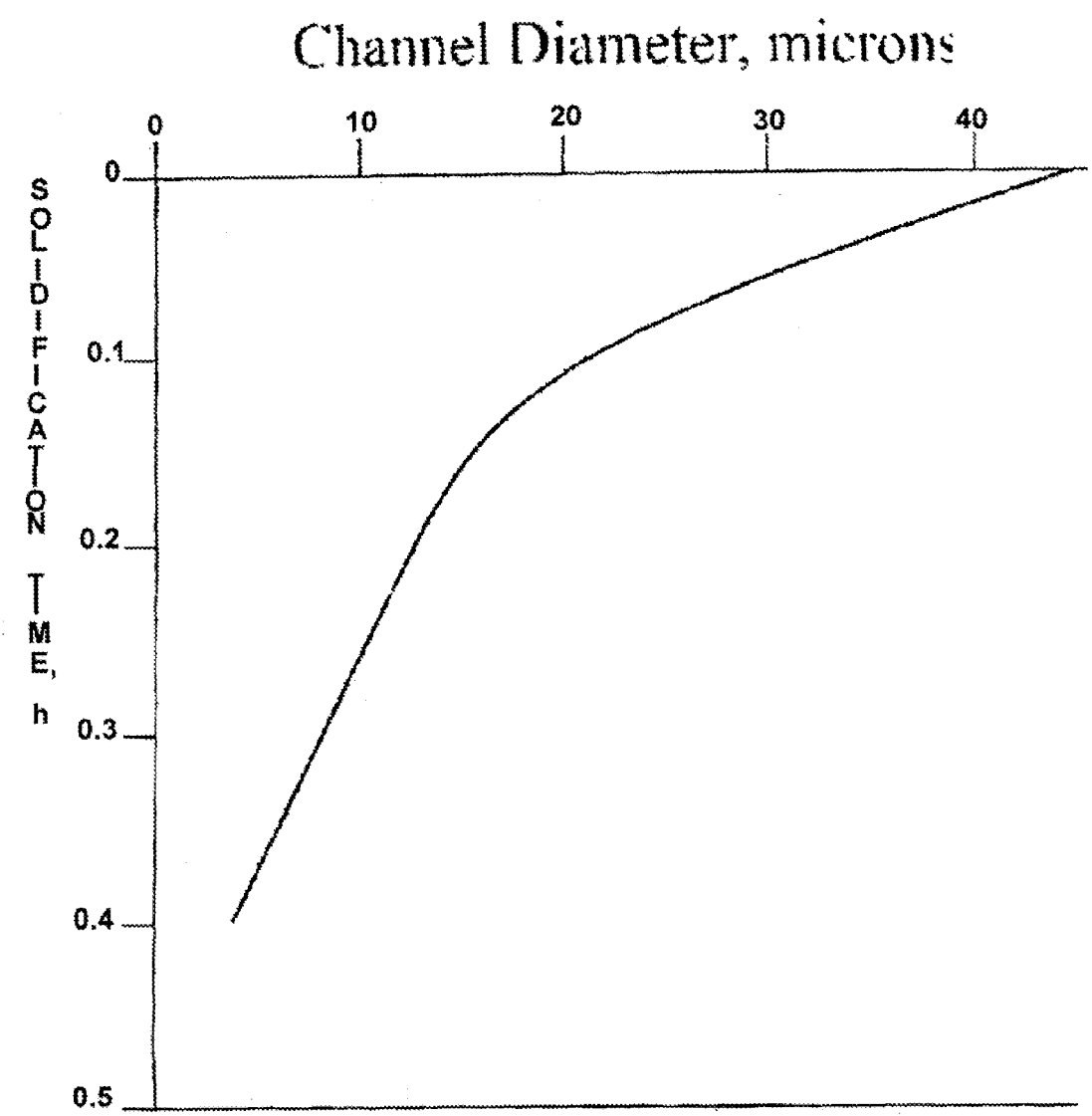
FIG. 12 is a further diagram illustrating the change of channel diameter during solidification.

As represented in FIG. 12, the solidification pressure can be increased from the beginning of bubble nucleation to the end of material solidification, resulting in conical microchannels in the element. FIG. 12 indicates channel diameter changing during solidification, with start pressure 0.01 MPa and at the end of solidification, the pressure is 0.45 MPa (other parameters was constant).

Experiments found that when the pressure starts at 0.01 MPa to 0.45 MPa, the time of solidification and the diameter of micro-channels are decreased significantly (FIG. 12). The present invention permits the production of a matrix with micro channel size from 1 μm to 300 μm. Thus, conducting chemical or biological reactions in ultra-narrow microchannels of porous materials permits the transport limitations across the unstirred layer for chemical and biological agents to be overcome. In addition, the reduction of physical size of flow cells to cross-sectional dimensions on the order of one to ten microns (microchannels) results in a large surface area to volume ratio and a decrease of the Nernst diffusion layer from 10 μm to 0.02 μm.

Since the magnitude of the diffusionally limited analytical signal of a sensor is inversely proportional to the thickness of the diffusion layer, the effects observed in microchannels may be explained by facilitated diffusion of analytes (antigen, antibody, conjugate, substrate, products of enzymatic reactions, etc.) from the bulk of the solution to the electrode surface. That is critical from point of view sensitivity and a time of assay.

Figure 13:
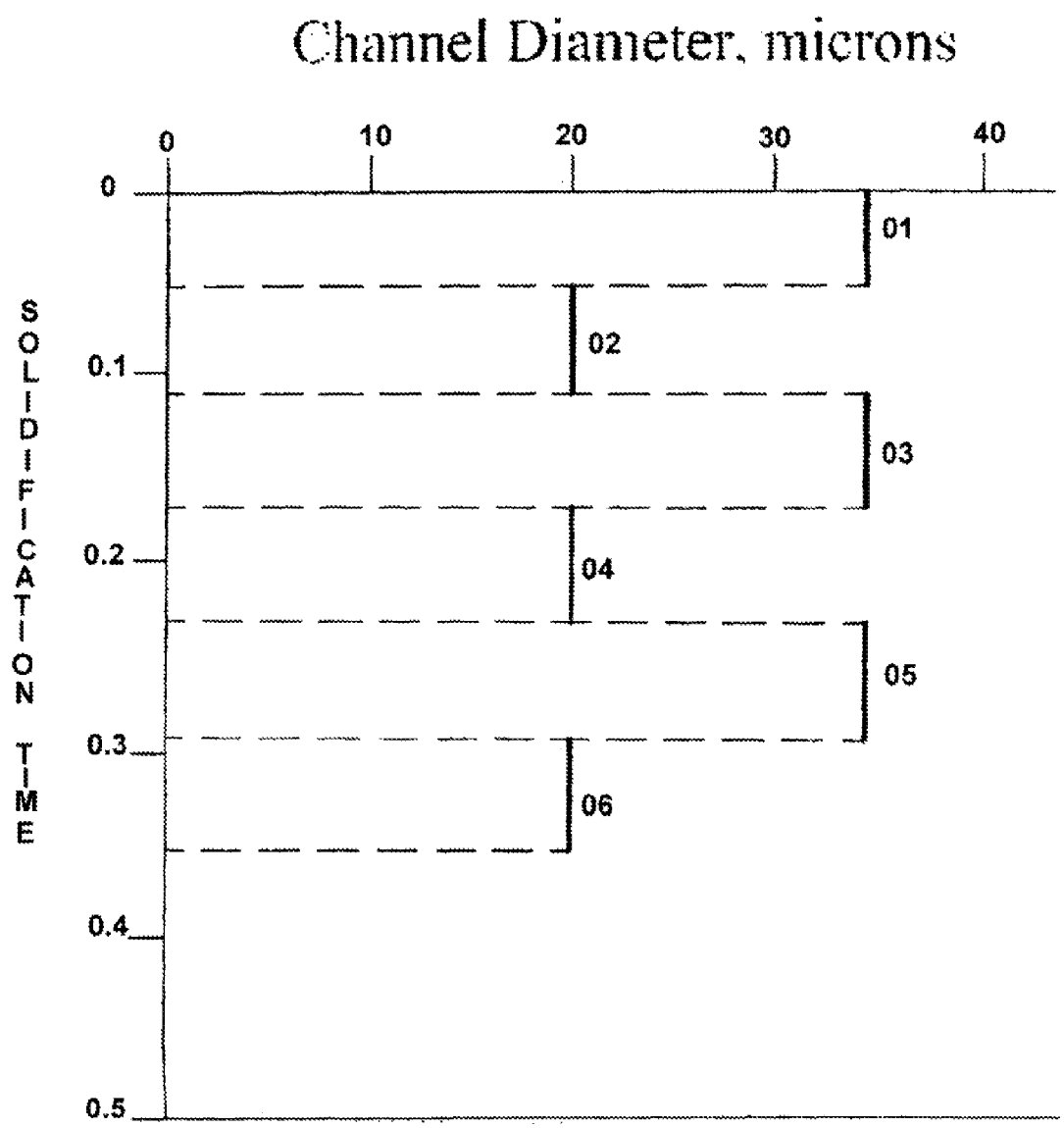
FIG. 13 is a diagram showing periodical convergent and dilative or corrugated microchannels in the element.

As illustrated in FIG. 13, the solidification pressure is pulsated during bubble growth, and the pressure change is greater than 10% of the solidification pressure, resulting in periodical convergent and dilative or corrugated microchannels in said element. FIG. 13 shows a diagram of obtaining periodical convergent and dilative or corrugated microchannels in the element: in periods 01, 03, 05, the total pressure is 0.05 MPa; in periods 02, 04, 06, the total pressure is 0.1 MPa.

Due to this approach a chaotic advection can be realized due to the modification of the shape and geometry of the channel to achieve splitting, stretching, folding and breaking of the flow there through. Thus, the micromixer created makes it possible to achieve a nearly homogeneous mixture in as little as one second, compared with 500 seconds for diffusion alone. In addition, a far greater flow rate through the micromixer is possible as compared to the slow rate required by prior art mixers.

Figure 14:
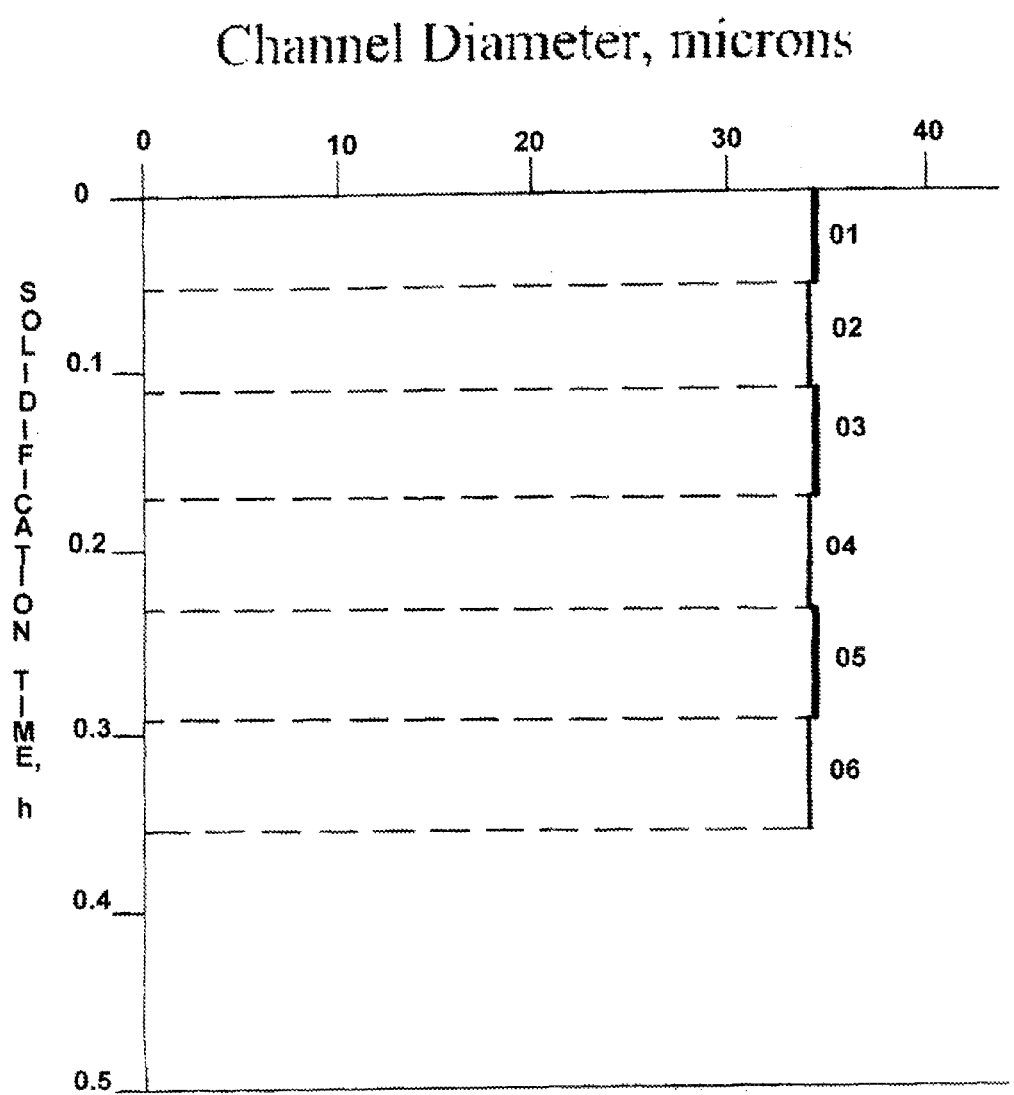
FIG. 14 is a further diagram showing periodical convergent and dilative or corrugated microchannels in the element.

FIG. 14 shows a diagram of obtaining periodical convergent and dilative or corrugated microchannels in said element: in periods 01, 03, 05, the total pressure is 0.05 MPa; in periods 02, 04, 06, the total pressure is 0.047 MPa.

Figure 15:
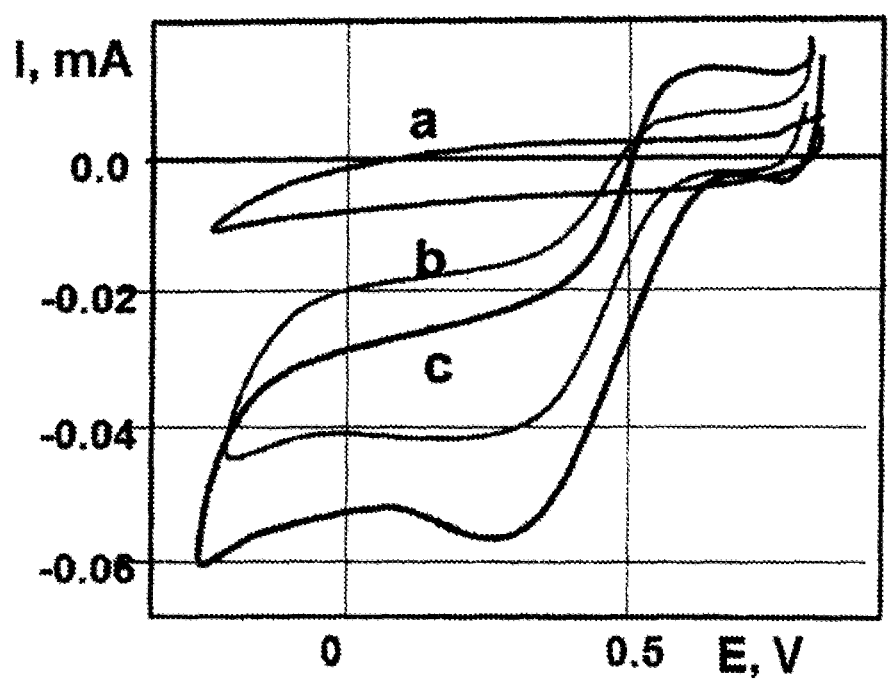
FIG. 15 is a diagram showing the cyclic voltammograms (CV) of immobilized laccase on several surfaces.

FIG. 15 illustrates cyclic voltammograms (CV) of laccase immobilized a) a non-porous gold electrode; b) porous carbon electrode modified with CNTs; and c) the surface of a multi-microchannel porous gold electrode.

Progress in nanoscience and nanotechnology has created an excellent basis for design and development of the next generation of biofuel cells based on direct electrical communication between the active site of enzymes and an electrode. Direct electron transfer (DET) between enzyme catalysts and electrode materials contributes significant design advantages in the construction of biofuel cells. A biofuel cell based on DET can theoretically operate in a single compartment cell, without exogenous electron transfer redox mediators, and at a potential approaching the redox potential of the enzyme itself. The electroreduction of dioxygen catalyzed by MCO, in the absence of mediators, has now been demonstrated on various electrode surfaces, but the power conversion efficiency remains inherently low. However, the main challenge is associated with engineering the enzyme/electrode interface to establish efficient electron transfer (ET) between redox center of enzyme and electrode.

The present invention shows for the first time that immobilization of enzyme molecules (laccase) on the wall surface of said microchannels (diameter of channels was between 1 μm and 20 μm) of gold electrode facilitates DET and bioelectrocatalytic oxygen reduction significantly.

For the proof of concept, the laccase from Trametes versicolor was immobilized directly on the said surface of multi-microchannel porous gold electrode. The enzyme immobilization efficiency was determined using standard biochemical assays. For control experiments, laccase was associated a) directly to non-porous gold electrode and b) to porous carbon electrode modified with carbon nanotubes (CNTs). Laccase adsorbed directly on gold electrode, showed no evidence of electrocatalytic activity for oxygen reduction ("a" in FIG. 15). Despite a theoretically short electron tunneling distance between the enzyme redox center and the electrode, the open circuit potential (OCP) for the oxygen reduction reaction was 0.31 V±0.03 (n=4), significantly lower than the thermodynamic potential (0.688 V vs Ag/AgCl). Carbon porous electrode modified with CNTs had a higher capacitance (higher electrochemical surface area) and increased OCP (0.49±0.02 V; n=3). Although the nanomaterial dimensions may bring about close physical binding between laccase and CNT that could facilitate electron tunnelling, there was not enough efficient direct electron transfer ("b" in FIG. 15).

When laccase was immobilized directly on the wall surface of said microchannels (diameter of channels was between 1 μm and 20 μm) of gold electrode, the cyclic woltammogram shown a very high electrocatalytic activity for oxygen reduction ("c" in FIG. 15). The cathodic sweep showed a huge oxygen reduction signal that has started from 0.6 V. The OCP, onset and half peak potentials were 0.60±0.01, 0.6±0.01, and 0.47±0.02 V (n=3), respectively and diffusion limitation conditions were reached at ~0.4 V during the cathodic sweep.

Thus, the efficiency of direct bioelectrocatalysis by using multi-microchannel technology was greater than previous reports for enzyme electrodes and may provide a significant advance for practical bio-electrocatalysis. Application of a multi-microchannel, flow-through element prepared according to the Shapovalov U.S. Pat. No. 5,181,549 for design and development of biofuel cells based on direct electron transfer can facilitate direct bioelectrocatalysis significantly.

DET provides the opportunity to simplify and miniaturize the construction of biofuel cells for integration into microscale sensor transmitter systems, pacemakers, and lab-on-a-chip devices.

The present invention is, of course, in no way restricted to the specific disclosure of the specification and drawings, but also encompasses any modifications within the scope of the appended claims.

We claim:

1. A method of using a multi-microchannel, flow-through element as a transducer or electrode in an electrochemical sensor, comprising:
    applying a polarization potential between the multi-microchannel, flow-through element as a working electrode and a further, reference electrode;
    exposing the multi-microchannel, flow-through element to a sample containing an analyte;
    detecting as a signal a physico-chemical change as a result of interactions between the analyte in the sample and a complementary biorecognition agent, wherein said complementary biorecognition agent is immobilized in real time on at least one surface of the multi-microchannel flow-through element,
    wherein the multi-microchannel, flow-through element is provided for use in an electrochemical sensor, and wherein the multi-microchannel, flow-through element is provided as a transducer and is an electrically conductive, metallic element,
    wherein the multi-microchannel, flow-through element includes a body and a plurality of microchannels, wherein each of said microchannels extends completely through the body of the multi-microchannel, flow-through element and provides a direct flow path between opposite faces of said multi-microchannel, flow-through element.

2. The method of claim 1, wherein the multi-microchannel, flow-through element includes a plurality of microchannels, and wherein walls of said microchannels of said multi-microchannel, flow-through element have a mirrored and smooth, unpolished, surface.

3. The method of claim 1, wherein a chemical or the biological recognition agent is immobilized on at least some of the walls of said microchannels of said multi-microchannel, flow-through element.

4. The method of claim 3, wherein said chemical or biological recognition agent is effective for carrying out binding reactions involving small molecules, macromolecules, particles or cellular systems.

5. The method of claim 3, wherein said chemical or biological recognition agents are selected from the group consisting of polypeptides, proteins, nucleic acids, receptors, polysaccharides, phospholipids, cells, tissue, nano-particles, selected from the group consisting of metallic, and or carbon nanotubes, with immobilized biological recognition agent, and related unnatural polymers of biological relevance.

6. The method of claim 1, wherein the electrochemical sensor is a flow-through amperometric detector coupled with a micropipette, wherein said at least one multi-microchannel, flow-through element is disposed in said amperometric detector.

7. The method of claim 1, wherein the electrochemical sensor is a flow-through micro-array chip that includes a carrier for said at least one multi-microchannel, flow-through element and a respective contact pad disposed on said carrier and electrically connected to said at least one multi-microchannel, flow-through element.

8. The method of claim 7, wherein a plate is disposed on at least part of said carrier and is provided with holes to receive a portion of said at least one multi-microchannel, flow-through element that extends beyond a surface of said carrier.

9. The method of claim 7, wherein at least one cap is provided on said carrier for distributing said sample to said at least one multi-microchannel, flow-through element.

10. The method of claim 1, wherein walls of said microchannels of the flow-through element have ridges, grooves, protuberances, or regular or irregularly changing cross-sections.

11. A method of using a multi-microchannel, flow-through element as a transducer or electrode in an electrochemical sensor, comprising:
   applying a polarization potential between the multi-microchannel, flow-through element as a working electrode and a further, reference electrode;
   exposing the multi-microchannel, flow-through element to a sample containing an analyte;
   detecting as a signal a physico-chemical change as a result of interactions between the analyte in the sample and a complementary biorecognition agent immobilized on at least one surface of the multi-microchannel flow-through element,
   wherein the multi-microchannel, flow-through element is provided for use in an electrochemical sensor, and wherein the multi-microchannel, flow-through element is provided as a transducer and is an electrically conductive, metallic element, and
   wherein the electrochemical sensor is a flow-through micro-array chip that includes a carrier for said at least one multi-microchannel, flow-through element and a respective contact pad disposed on said carrier and electrically connected to said at least one multi-microchannel, flow-through element.

* * * * *